US006553094B1

(12) United States Patent
Bernardi et al.

(10) Patent No.: US 6,553,094 B1
(45) Date of Patent: Apr. 22, 2003

(54) METHOD OF DETERMINING A CONTENT OF A NUCLEAR WASTE CONTAINER

(75) Inventors: Richard T. Bernardi, Prospect Heights, IL (US); David Entwistle, Buffalo Grove, IL (US)

(73) Assignee: Bio-Imaging Research, Inc., Lincolnshire, IL (US)

( * ) Notice: Subject to any disclaimer, the term of this patent is extended or adjusted under 35 U.S.C. 154(b) by 8 days.

(21) Appl. No.: 09/648,676

(22) Filed: Aug. 25, 2000

(51) Int. Cl.[7] ............................................... G01N 23/04
(52) U.S. Cl. ............................... 378/57; 378/4; 378/21
(58) Field of Search ............................ 378/57, 88, 4, 378/21, 22, 23, 901

(56) References Cited

U.S. PATENT DOCUMENTS 5,164,971 A * 11/1992 Peyret et al. .................. 378/4
5,400,381 A * 3/1995 Steude et al. ................ 378/57
6,370,222 B1 * 4/2002 Cornick, Jr. ................. 378/57

* cited by examiner

Primary Examiner—Drew A. Dunn
Assistant Examiner—Courtney Thomas
(74) Attorney, Agent, or Firm—Welsh & Katz, Ltd.

(57) ABSTRACT

A method and apparatus are provided for identifying contents of a nuclear waste container. The method includes the steps of forming an image of the contents of the container using digital radiography, visually comparing contents of the image with expected contents of the container and performing computer tomography on the container when the visual inspection reveals an inconsistency between the contents of the image and the expected contents of the container.

26 Claims, 5 Drawing Sheets

METHOD OF DETERMINING A CONTENT OF A NUCLEAR WASTE CONTAINER

This invention was made with Government support under Contract No. DE-FG02-90ER80893 awarded by the Department of Energy. The Government has certain rights in this invention.

FIELD OF THE INVENTION

The field of the invention relates to nuclear waste and more particularly to methods of determining a content of nuclear waste containers.

BACKGROUND OF THE INVENTION

Since the advent of the nuclear age, nuclear waste has been a significant impediment to the development of nuclear technology. In the last fifty years, nuclear waste has accumulated in significant quantities.

Nuclear waste is different than other types of waste in that it can kill without direct contact through the effects of radiation. Because of radiation, nuclear waste must be either shielded or stored in protected areas.

While shielding is effective, it also creates additional difficulty in storing and moving waste containers. It also adds to the bulk of storage containers.

When nuclear energy first became a factor during World War II (and to a lesser extend even now) nuclear waste was handled in a manner similar to other wastes. What makes nuclear waste more difficult to process than other wastes, however, is the difficulty of identifying and classifying the contents of nuclear waste containers.

In the past, the accepted method for identification of container content has relied upon the non-destructive examination of nuclear waste drums using x-ray inspection and real-time radiography (RTR). Standard RTR techniques have included the use of 450 kV (or less) constant potential x-ray sources. Image intensifiers have been used as live radiographic detectors for the video taping of drum content.

The use of RTR could be improved by varying the x-ray voltages and currents to optimize the viewing contrast for differing drum content. However, RTR still has limited inspection capability for the imaging of dense waste drum content like metals, cements and sludge because of the lack of x-ray penetration at 450 kV and a lack of dynamic range for an image intensifier of the x-ray detector. To aid in the analysis of nuclear waste, the Department of Energy (DOE) has published a number of procedures explaining the use of RTR for inspection for nuclear waste drums.

The limitations of RTR methods may be discerned from a recent RCRA permit from the state of New Mexico for the DOE's WIPP site. The permit states that drums, which cannot be inspected by RTR (e.g., lead lined drums) must be opened for direct invasive inspection by visual examination. Invasive examination is much more costly than the method discussed below because of the need for operator protection from radiation using a protective enclosure (e.g., a glove box).

Since WWII thousands of nuclear waste containers have been filled and stored in a limited number of locations without regard to what such containers have stored inside them. In order to resolve the problem of nuclear waste, an effort must be made to classify nuclear waste as a first step in finding a final solution to disposal of such waste. Accordingly, a need exists for a safe and more reliable means of identifying and classifying nuclear waste.

SUMMARY

A method and apparatus are provided for identifying a content of a nuclear waste container. The method includes the steps of forming an image of the contents of the container using digital radiography, visually comparing a content of the image with an expected content of the container and performing computer tomography on the container when the visual inspection reveals an inconsistency with the expected content.

DETAILED DESCRIPTION OF A PREFERRED EMBODIMENT

Figure 1:
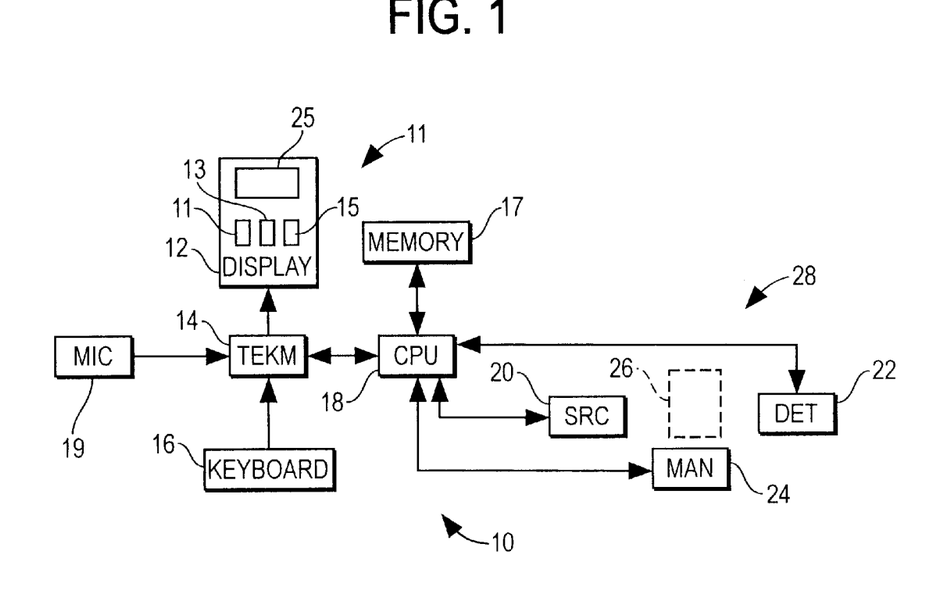
FIG. 1 is a block diagram of a waste inspection tomographic system in accordance with an illustrated embodiment of the invention.

To overcome the above limitations of RTR for inspection of nuclear waste drums, the waste inspection tomography (WIT) system 10 of FIG. 1 incorporates the needed hardware and x-ray inspection methods that together can successfully examine and identify the contents of nuclear waste drums from the lower density waste matrices to the higher density and heavier waste of larger drums. This unique capability to inspect all or most nuclear waste drums with the same instrument 10 along with the methods and hardware employed are discussed in detail below.

FIG. 1 is a block diagram of a system 10 for identifying nuclear waste in accordance with an illustrated embodiment of the invention. Under the illustrated embodiment, a container (e.g., a barrel) 26 of nuclear waste is placed upon a manipulator 24 which functions to move the container 26 through an imaging field 28. The imaging field 28 includes a high energy (e.g., x-ray) source 20 and array of detectors 22.

Figure 9:
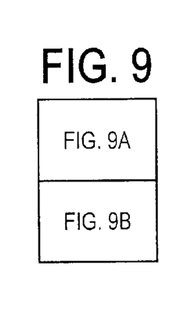
FIG. 9 is a flow chart of process steps that may be used by the system of FIG. 1.
Figure 9A:
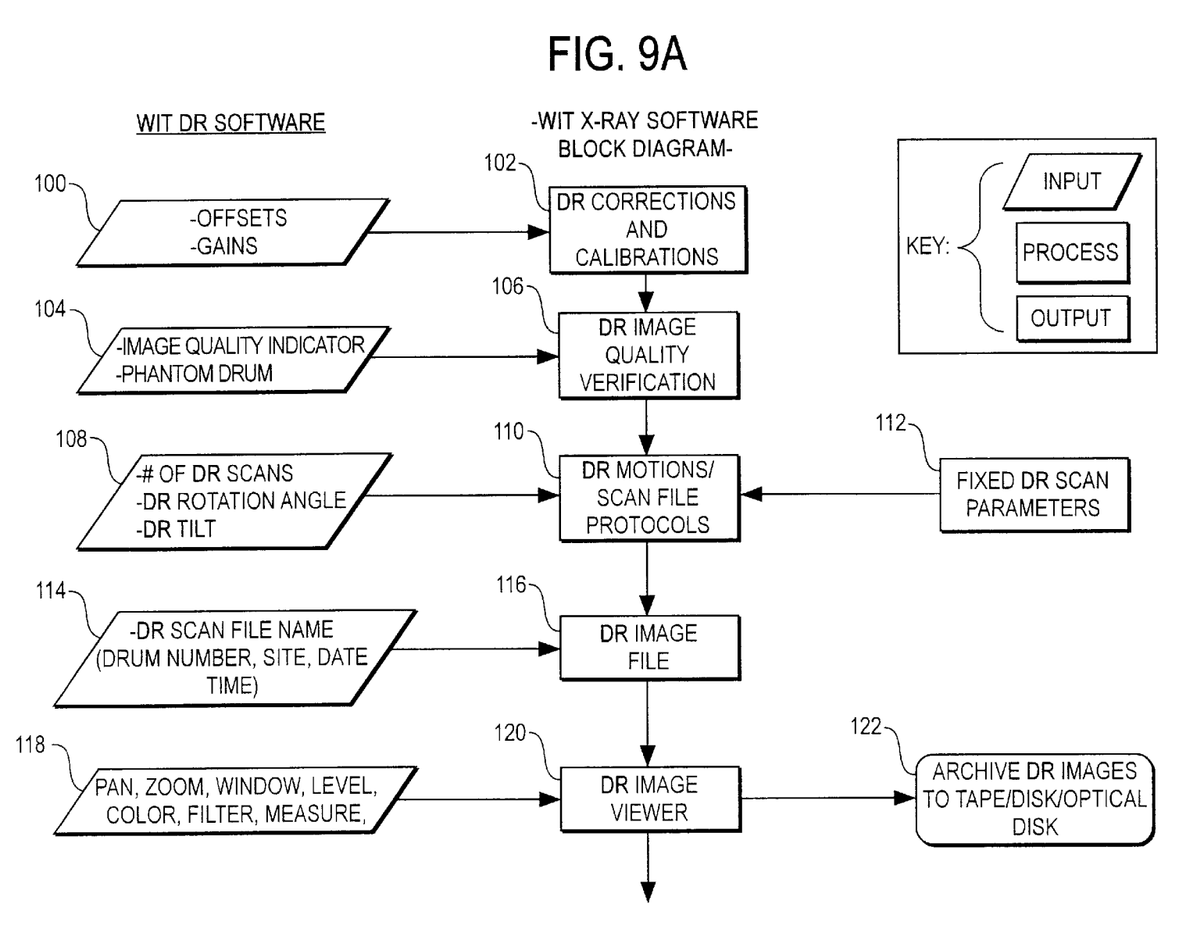
Figure 9B:
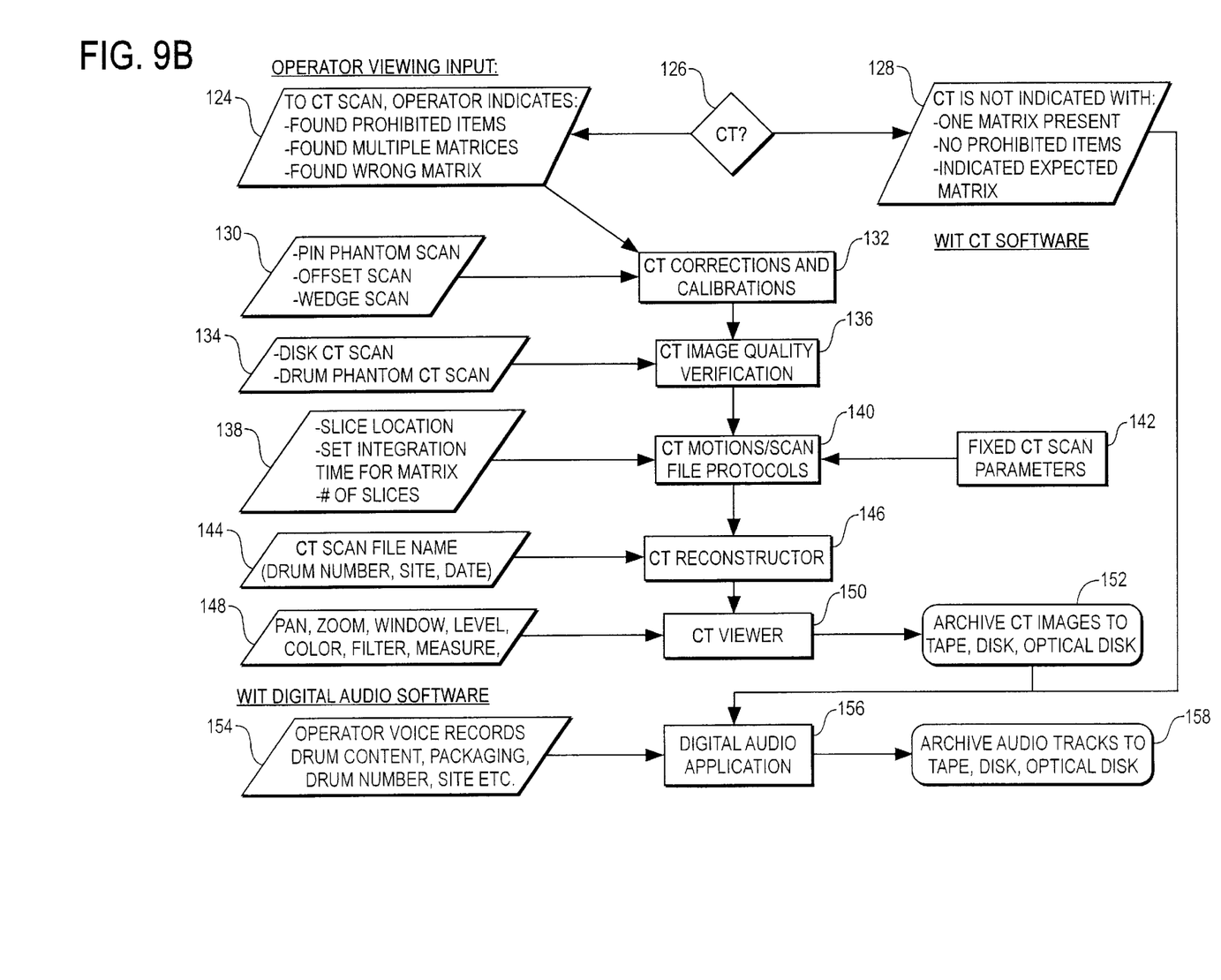

FIG. 9 is a flow chart of process steps that may be used by the system of FIG. 1. FIG. 9 may be referred to as appropriate to an understanding of the system of FIG. 1.

The manipulator 24, source 20 and detector 22 of the imaging field 28 operate under control of a central processing unit (CPU) 18. The CPU 18 operates under control of an operators station 11. The operators station 11 includes a terminal 14 with a display 12 and input device (e.g., a keyboard) 16.

Figure 2:
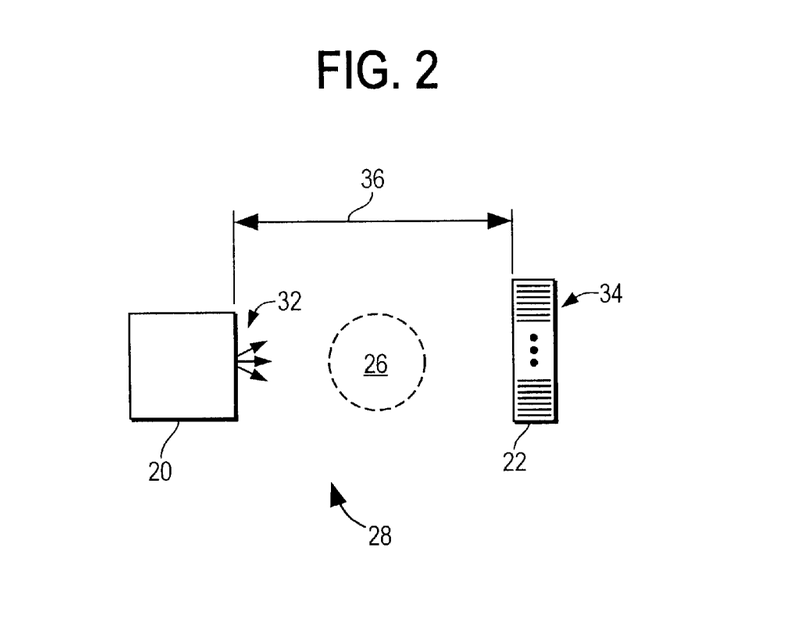
FIG. 2 depicts the imaging structure used by the system of FIG. 1.
Figure 7:
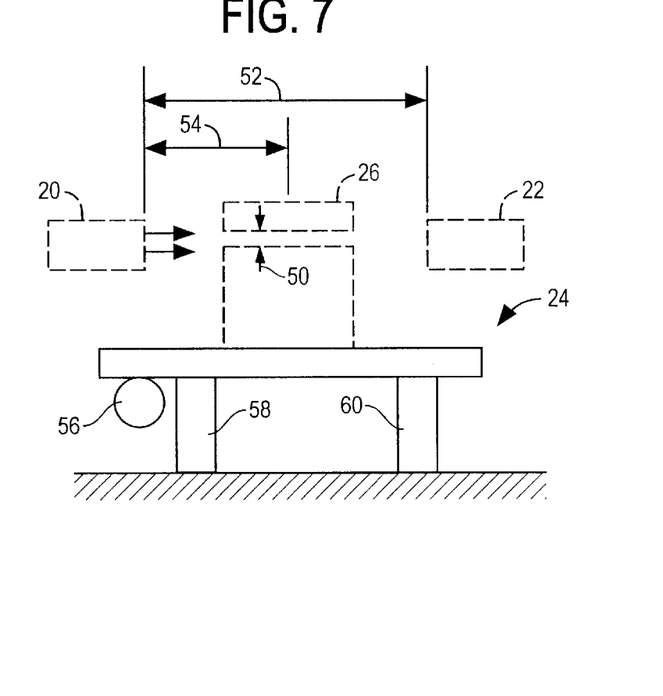
FIG. 7 is a side view of the imaging structure and container manipulator of the system of FIG. 1.

The WIT system 10 may use a 2 MV pulsed high-energy radiation source (e.g., linear accelerator or Linac) 20 with an output collimated to a stationary horizontal fan beam 32 of x-rays. The detectors 22 may consist of a stationary horizontal linear array of 2 MV x-ray detector elements 34 (e.g., 896 channels) collimated for receiving a horizontal fan beam of x-rays (see FIGS. 2 and 7). The desired performance of the invention provides a digital radiography (DR) and computed tomography (CT) inspection method suitable for nuclear waste drum inspection of all expected waste matrices and drum packages.

Figure 3:
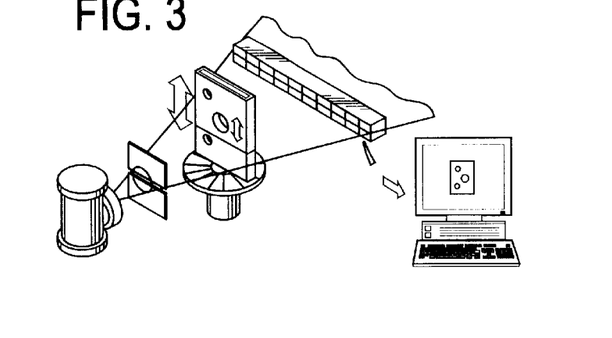
FIG. 3 depicts an object, such as a drum, located on a circular turntable of the system of FIG. 1 that is vertically moved through a stationary fan beam of x-rays while the system projects a radiographic image of the object, line by line, using a linear array of x-ray detectors.
Figure 4:
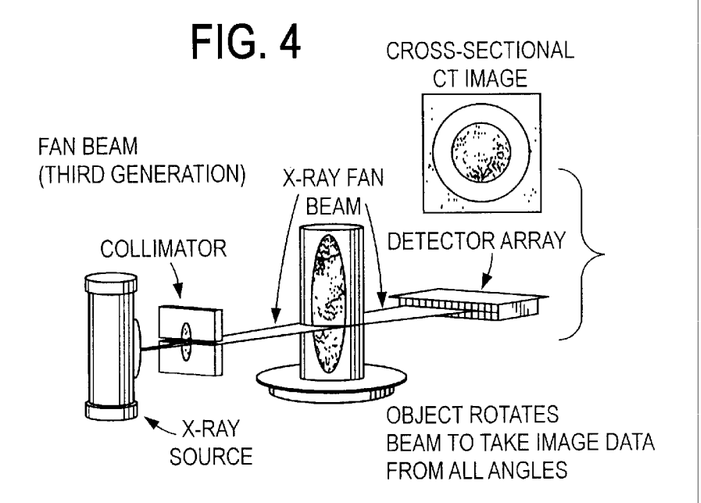
FIG. 4 depicts a waste drum rotated on the turntable while a stationary fan beam of x-rays passes through the drum for collection by a stationary array of detectors which are connected to a computer system which is designed to reconstruct a cross sectional slice of the waste drum as a CT image.

The waste drum may be placed on a 3-axis manipulator 24 for drum motion. The drum motion includes elevation, rotation and tilt. Elevation is used in DR to collect line by line data (e.g., using detector integration) to produce a projection x-ray image of a drum as shown in FIG. 3. The resulting DR image is 896 pixels wide by 900 pixels high with an effective pixel size of about 1 mm by 1 mm in the resulting DR image.

Figure 5:
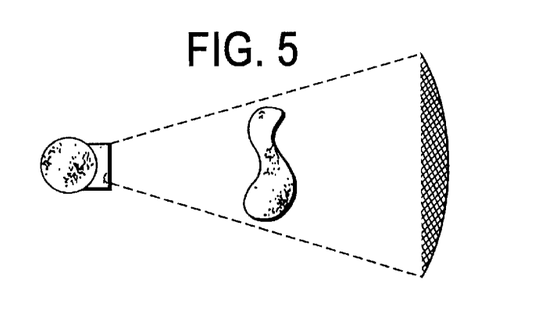
FIG. 5 depicts a waste container which is completely covered by the fan beam of x-rays used by both DR and CT and detectors which must accept x-rays in an unattenuated path outside the object and from the thickest and densest part of the container to be inspected.
Figure 6:
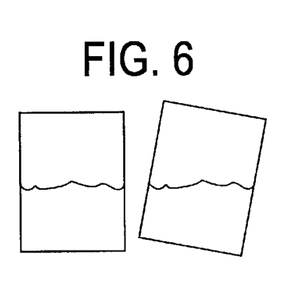
FIG. 6 depicts two separate DR views from the system of FIG. 1 where the view of the left is an untilted view of a drum and the view on the right is a view of the drum tilted by about 4 degrees for purposes of detecting the presence of free liquid.

Rotation of the drum 26 is used in the CT mode to collect a CT slice using an appropriate CT process (e.g., a third generation CT method) as shown in FIG. 5. The geometry used by the manipulator 24 of the system 10 allows the drum 26 to be placed in the middle of the fan beam 32, which may be used for both CT and DR as is shown in FIG. 5.

The third axis of motion, is the tilt axis, which provides a drum tilt of typically 3 to 4 degrees. Tilt is used to identify whether liquids are present in the drum by presenting the DR image of the "tilted" drum 26 (and/or any container within the drum 26) on the display 12. Identification of liquid may be accomplished by a comparison of the tilted and non-tilted images side by side (or with the images paged back to back) and observing for any indication of a liquid surface that remains horizontal in both the tilted and non-tilted images.

The total resulting drum images produced by the process described herein include non-tilted DR images, tilted DR images and CT images, which are together used for the identification of the contents of nuclear waste drums. The described x-ray methods used by WIT require specific x-ray techniques described below that result in the successful inspection of the wide variety of nuclear waste drum contents and matrices.

DR images may be obtained of waste containers 26, including 55 gallon drums, 85 gallon drums or 110 gallon drums. Waste drums 26 full of sludge may have a weight of up to or exceeding 1600 pounds. The WIT x-ray scanner 28 may have physical capacity to handle a maximum drum size of 110 gallons and a weight of up to or exceeding 1600 pounds.

The DR and CT scans may have a typical x-ray fan beam thickness 50 (FIG. 7) of 10 mm within the drum. A distance 52 between the source 20 and detector 34 may be 100 mm. A distance 54 from the source 20 to the drum center of rotation may be 50 inches. A voltage of the Linac within the source 20 may be 2 MV. The Linac output may be 72 Rads at one meter.

The Linac pulse rate may be 250 pulses per second. At 250 pulses per second, each line of the DR scan may be completed in 4 milliseconds. A time for each line of the CT scan may be adjusted based upon a density of the drum 26.

As mentioned above, 900 horizontal lines may be collected for a full DR scan. A first DR image is collected at a first position of the drum 26. The drum 26 may then be rotated 90 degrees around a vertical axis and a second DR image may be collected.

A focal spot size of the x-ray source may be 1.5 mm for both the DR scans and the CT scan. The number of x-ray detectors (as mentioned above) may be 896. The pitch of the detectors (channel to channel space) may be 1.38 mm. The dead space thickness between channels (between detectors) may be 0.58 mm. An active width of each detector channel may be 0.8 mm.

Based upon the above conditions, a single DR data line may be collected (integrated) in 64 milliseconds. In total, 900 data lines are collected to cover the full height of a drum 26. A total time for a DR scan may be 57 seconds. To completely inspect a waste drum 26, three DR images may be collected: one at zero degrees rotation, one at ninety degrees rotation and one at 3–4 degrees of tilt.

The criteria used to indicate whether further radiography through CT is necessary may be based upon the operator's interpretation of the DR images. Three criteria may be used to determine the need for CT. CT may be required where multiple matrices are present. Multiple matrices in this context means that there are at least two matrices within the DR images and that one is superpositioned over the other, resulting in an inability to read either matrix. In the case of superpositioned matrices, CT would be required to interpret the contents of the matrices.

A second reason to resort to CT is where the contents of drum 26 do not match an expected content. In this case, a manifest of the drum 26 is compared against the DR images for inconsistencies (e.g., a different matrix, combustibles instead of metals, etc.).

A third reason for CT may be the presence of prohibited items within the drum 26. A prohibited item may be any item (e.g., free liquids, aerosol can, etc.) not allowed within the drum 26.

The process of determining whether a drum must be further processed (using CT to determine its contents) begins with the operator's review of the DR image. The operator visually compares the DR images with an expected contents of the drum to determine the need for further CT imaging.

The three criteria will now be discussed in more detail. The first criteria of multiple matrices may be considered first. As used herein, a matrix means a relatively solid aggregate of dissimilar materials. For example, radioactive debris encased in concrete. A matrix may also be a wad of paper or plastic that may not be readily identifiable from the DR image.

In the case of multiple matrices, CT imaging may be required where (because of the positioning of the images) superpositioning prevents a clear view of any one of the matrices. Where a clear view of each of the multiple matrices is available, then CT imaging may not be necessary.

Combustibles (e.g., paper, plastic, wood, etc.) may be identified from the characteristics of the DR image. For example, wrinkling is a characteristic of plastic and/or paper that (when found) may be used as an indication of the presence of such materials. The relatively faint signature of paper or plastics (or wood) may also be used as further indication of such materials.

As used herein, the step of visually comparing a content of the nuclear waste drum with an expected contents includes two-steps. First, the DR image is compared with a written description (i.e., the manifest) of drum contents. The manifest must be a description (e.g., a list) of drum content that was prepared contemporaneously with the filling of the drum. Where the manifest does not match the drum contents then an inconsistency exists and CT imaging may be required. As used herein, an inconsistency means a deviation from the DOE's minimum requirement of acceptable knowledge of the contents of a waste drum or, alternatively, it means the presence of prohibited items.

In some cases, a manifest may not be complete or may be missing entirely. Where a manifest exists, the DR images may be used in conjunction with the manifest to identify inconsistencies. Where a manifest is missing (or is incomplete), then an inconsistency exists with regard to any item found in the drum.

The second step of the visual comparison may involve a visual search of the DR images for prohibited items (e.g., liquids, aerosol cans, etc.). Where prohibited items are found, an inconsistency exists with regard to DOE rules for waste containers and a CT scan is performed.

Once an inconsistency is identified, a location for CT imaging may be determined. CT may be performed over the entire volume of the container 26 or only of the limited volume that provides the basis of the inconsistency. Up to 90 slices may be scanned for CT imaging, with a CT slice width of 10 mm. Typical CT reconstruction sizes may be 256×256, 512 ×512 or 1024×2024 pixels. The maximum number of CT views may be 944. The diameter for the CT field of views may be 844 mm for a 110 gallon drum, 822 mm for a 85 gallon drum or 800 mm for a 55 gallon drum.

In order to perform CT, the operator may first estimate a density of the container 26 based upon the DR images and then select a scan time for each rotation based upon the observed density. A time of 8 seconds (8 milliseconds integration per view and 2 Linac pulses per view) may be chosen for a drum 26 of less than 250 pounds and light weight matrices such as combustibles. A time of 30 seconds (32 milliseconds integration and 8 Linac pulses per view) may be chosen for a drum 26 of 250–500 pounds and heavy matrices such as metals or cements. A time of 60 seconds (64 milliseconds integration and 16 Linac pulses per view) may be chosen for a drum 26 of greater than 500 pounds and heavy matrices such as metals or cement.

A detailed example will now be provided illustrating a preferred method of use of the system 10. The operator may begin by setting up the system 10. A set of offsets and gains may be selected 100 (FIG. 9) for the container 26 to be analyzed. The offsets and gains may be used to calibrate 102 the system 10 for use with the container 26.

An image quality indicator and a phantom drum file identifier 104 may be entered through the keyboard 16. The entered values may be used to verify 106 operation of the system 10.

The number of DR scans, DR rotation angle, and DR tilt of the drum 26 may be entered 108. A set of fixed DR scan parameters may be recovered 112 from memory 17. The entered motion values may be used to set up 110 the DR motion and scan file protocols.

The operator may be asked to enter 114 a DR scan file name, including a drum number, site, date and time. The CPU 18 may use such information to open 116 a DR image file.

Next, the operator may be asked to enter 118 any special pan, zoom, window, level, color, filter, or measure parameters. The operator may also identify 122 a file destination.

Under the illustrated embodiment, the CPU 18 first collects a first DR scan line at a first position at zero degrees rotation of the drum 26 and the elevators in a fully lowered position. The elevators 58, 60 may be activated to raise the drum 26 and another line is collected. This process may be repeated until the 900 lines of a first DR image have been collected.

A rotation motor 56 may be activated to rotate the drum 26 ninety degrees and the process may be repeated to collect a second DR image. One of the elevators 58, 60 may be activated to tilt the drum 26 by 3–4 degrees and a third DR image may be collected.

The CPU 18 may present 120 the images on the display 12. The operator may then view the first, second and third images 11, 13, 15 side-by-side on a display 12. Alternately, the operator may switch back and forth to interpret the images.

Where no inconsistencies are found 128, the CPU 18 may archive 152 the images. The operator may also include a voice recording of any observed anomalies by speaking 154 into a microphone 19. A digital audio application converts 156 the voice into a digital format which may then be stored 158 along with the images.

Where inconsistencies are found 126, the operator may initiate a CT scan. To initiate a scan, the operator may first select 130 a type of scan. Using the selected type of scan, the CPU 18 may access an appropriate file and recover 132 an appropriate set of corrections and calibrations.

The operator may also select 136 a set of calibration features. To calibrate the system 10, the operator may enter 134 an identifier of a disk scan or phantom drum CT scan. The CPU 18 may process the calibration information which may be corrected 136 as needed by the operator.

Figure 8:
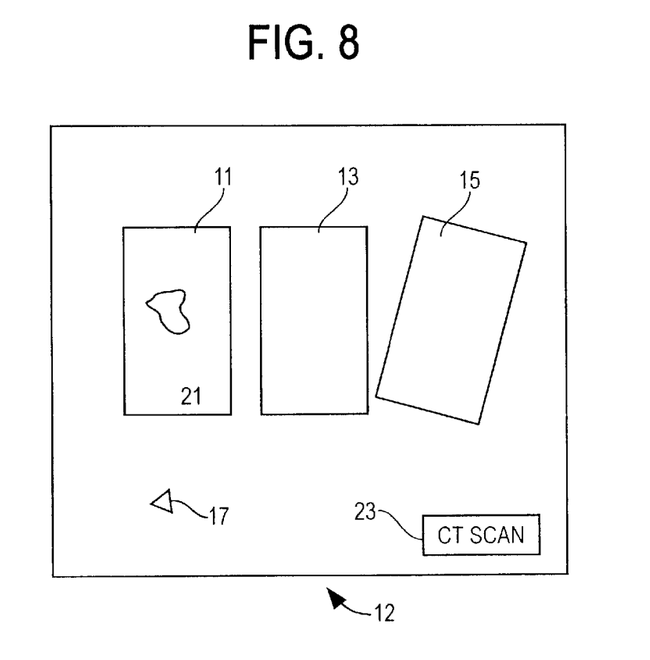
FIG. 8 depicts DR images of the system of FIG. 1 that may be reviewed by an operator for inconsistencies.

To initiate the scan, the operator may place a cursor 17 (FIG. 8) over a matrix 21 or other artifact and activate 124 a switch (not shown) on the cursor 17 to mark 138 slices or groups of slices. Alternatively, the operator may elect 142 to scan a predetermined portion or the entire drum 26.

Following the designation of selected portions, the operator may enter 144 drum identifiers and activate a softkey 23 to initiate the CT scan. The CPU 18 may then execute 140 the CT scan of the designated portions.

Following the CT scan, selected slices 25 may be reconstructed 146 by a CT reconstructor and displayed on the display 12. The displayed image 25 may be moved up or down through the selected area of the drum by operation of the cursor 17. The operator may change 148 an orientation or perspective of a slice using methods well known in the CT arts. Following a review of the CT images 25, the operator may archive 152 the results.

A specific embodiment of a method and apparatus for determining a content of a nuclear waste container according to the present invention has been described for the purpose of illustrating the manner in which the invention is made and used. It should be understood that the implementation of other variations and modifications of the invention and its various aspects will be apparent to one skilled in the art, and that the invention is not limited by the specific embodiments described. Therefore, it is contemplated to cover the present invention and any and all modifications, variations, or equivalents that fall within the true spirit and scope of the basic underlying principles disclosed and claimed herein.

What is claimed is:

1. A method of identifying contents of a nuclear waste container, such method comprising the steps of:

forming an image of the contents of the nuclear waste container using digital radiography;

visually comparing contents of the image with expected contents of the container; and performing a CT scan on the nuclear waste container and forming at least one tomographic image, but only when the visual inspection reveals an inconsistency between the contents of the image and the expected contents of the container.

2. The method of identifying a content of a nuclear waste container as in claim 1 wherein the step of forming an image using digital radiography further comprises forming a first and second DR image from orthogonal perspectives.

3. The method of identifying a content of a nuclear waste container as in claim 1 wherein the step of forming an image using digital radiography further comprises tilting the container.

4. The method of identifying a content of a nuclear waste container as in claim 3 wherein the step of tilting the container further comprises forming an image of the tilted container.

5. The method of identifying a content of a nuclear waste container as in claim 4 wherein the step of forming an image of the tilted container further comprises detecting a liquid within the container based upon corresponding horizontal transition lines found within the tilted and untilted images of the container.

6. The method of identifying a content of a nuclear waste container as in claim 1 further comprising determining the expected content of the container by reading a manifest of container contents prepared at a time of filling of the nuclear waste container.

7. The method of identifying a content of a nuclear waste container as in claim 6 wherein the step of visually comparing a content of the image with an expected content of the container further comprises identifying visual elements of the formed images as items found within the manifest.

8. The method of identifying a content of a nuclear waste container as in claim 7 wherein the step of identifying visual elements of the formed images as items found within the manifest further comprises determining that an inconsistency exists when an item found within the image does not match any item listed on the manifest.

9. The method of identifying a content of a nuclear waste container as in claim 7 wherein the step of determining that an inconsistency exists further comprises finding multiple superpositioned matrices within the formed images.

10. The method of identifying a content of a nuclear waste container as in claim 7 wherein the step of determining that an inconsistency exists further comprises finding a prohibited item within the formed image.

11. The method of identifying a content of a nuclear waste container as in claim 1 wherein the step of performing the CT scan on the nuclear waste container and forming the tomographic image further comprises choosing a scan time for the computed tomography based upon a perceived density of any inconsistent item of the formed image.

12. An apparatus for identifying contents of a nuclear waste container, such apparatus comprising:
    means for forming an image of the contents of the nuclear waste container using digital radiography;
    means for visually comparing contents of the image with expected contents of the container; and means for performing a CT scan on the nuclear waste container and forming at least one tomographic images but only when the visual inspection reveals an inconsistency between the contents of the image and the expected contents of the container.

13. The apparatus for identifying a content of a nuclear waste container as in claim 12 wherein the means for forming an image using digital radiography further comprises means for forming a first and second DR image from orthogonal perspectives.

14. The apparatus for identifying a content of a nuclear waste container as in claim 12 wherein the means for forming an image using digital radiography further comprises means for tilting the container.

15. The apparatus for identifying a content of a nuclear waste container as in claim 14 wherein the means for tilting the container further comprises means for forming an image of the tilted container.

16. The apparatus for identifying a content of a nuclear waste container as in claim 15 wherein the means for forming an image of the tilted container further comprises means for detecting a liquid within the container based upon corresponding horizontal transition lines found within the tilted and untilted images of the container.

17. The apparatus for identifying a content of a nuclear waste container as in claim 12 further comprising means for determining the expected content of the container by reading a manifest of container contents prepared at a time of filling of the nuclear waste container.

18. The apparatus for identifying a content of a nuclear waste container as in claim 17 wherein the means for visually comparing a content of the image with an expected content of the container further comprises means for identifying visual elements of the formed images as items found within the manifest.

19. The apparatus for identifying a content of a nuclear waste container as in claim 18 wherein the means for identifying visual elements of the formed images as items found within the manifest further comprises means for determining that an inconsistency exists when an item found within the image does not match any item listed on the manifest.

20. The apparatus for identifying a content of a nuclear waste container as in claim 18 wherein the means for determining that an inconsistency exists further comprises means for finding multiple superpositioned matrices within the formed images.

21. The apparatus for identifying a content of a nuclear waste container as in claim 18 wherein the means for determining that an inconsistency exists further comprises means for finding a prohibited item within the formed image.

22. The apparatus for identifying a content of a nuclear waste container as in claim 12 wherein the means for performing the CT scan on the nuclear waste container to form the tomographic image further comprises means for choosing a scan time for the computed tomography based upon a perceived density of any inconsistent item of the formed image.

23. An apparatus for identifying contents of a nuclear waste container, such apparatus comprising:
    an x-ray viewer adapted to form an image of the contents of the nuclear waste container using digital radiography;
    a display adapted to visually compare contents of the image with expected contents of the container; and
    an x-ray source adapted to scan the container to form at least one tomographic image, but only when the visual inspection reveals an inconsistency between the contents of the image and the expected contents of the container.

24. The apparatus for identifying a content of a nuclear waste container as in claim 23 wherein the x-ray viewer further comprises first and second windows adapted to form a first and second DR image from orthogonal perspectives.

25. The apparatus for identifying a content of a nuclear waste container as in claim 24 wherein the first and second windows further comprises a third window adapted to show a tilted view of the container.

26. The apparatus for identifying a content of a nuclear waste container as in claim 23 wherein the x-ray source further comprises an input device adapted to allow the choosing of a scan time for a computed tomography scan based upon a perceived density of any inconsistent item of the formed image.

* * * * *